US010828464B2

(12) United States Patent
Rosenberg et al.

(10) Patent No.: US 10,828,464 B2
(45) Date of Patent: Nov. 10, 2020

(54) SYSTEMS AND METHODS FOR ANCHORING MEDICAL DEVICES

(71) Applicant: INTERRAD Medical, Inc., Plymouth, MN (US)

(72) Inventors: Michael S. Rosenberg, Eagan, MN (US); Mark R. Christianson, Plymouth, MN (US)

(73) Assignee: INTERRAD Medical, Inc., Plymouth, MN (US)

( * ) Notice: Subject to any disclaimer, the term of this patent is extended or adjusted under 35 U.S.C. 154(b) by 1096 days.

(21) Appl. No.: 15/207,628

(22) Filed: Jul. 12, 2016

(65) Prior Publication Data

US 2016/0317787 A1   Nov. 3, 2016

Related U.S. Application Data

(62) Division of application No. 13/766,102, filed on Feb. 13, 2013, now Pat. No. 9,415,190.

(51) Int. Cl.
*A61M 25/02*   (2006.01)

(52) U.S. Cl.
CPC ....... *A61M 25/02* (2013.01); *A61M 2025/024* (2013.01); *A61M 2025/0206* (2013.01); *A61M 2025/028* (2013.01); *A61M 2025/0286* (2013.01)

(58) Field of Classification Search
None
See application file for complete search history.

(56) References Cited

U.S. PATENT DOCUMENTS

| | | | |
|---|---|---|---|
| 3,039,468 A | 6/1962 | Price | |
| 3,765,032 A | 10/1973 | Palma | |
| 3,856,009 A | 12/1974 | Winnie | |
| 3,896,527 A | 7/1975 | Miller et al. | |
| 3,938,529 A | 2/1976 | Gibbons | |
| 4,043,346 A | 8/1977 | Mobley et al. | |
| 4,114,618 A | 9/1978 | Vargas | |
| 4,164,943 A | 8/1979 | Hill et al. | |
| 4,248,224 A | 2/1981 | Jones | |
| 4,309,994 A | 1/1982 | Grunwald | |
| 4,397,647 A | 8/1983 | Gordon | |
| 4,474,569 A | 10/1984 | Newkirk | |
| 4,569,344 A | 2/1986 | Palmer | |
| 4,592,356 A | 6/1986 | Gutierrez | |

(Continued)

FOREIGN PATENT DOCUMENTS

| WO | WO 199115254 | 10/1991 |
|---|---|---|
| WO | WO 1997/039790 | 10/1997 |

(Continued)

OTHER PUBLICATIONS

Johnson & Johnson web page printout, "The EndoANCHOR Comparative Summary" printed Sep. 13, 2005, 2 pages.

(Continued)

*Primary Examiner* — Rebecca E Eisenberg
*Assistant Examiner* — Weng Lee
(74) *Attorney, Agent, or Firm* — Fish & Richardson P.C.

(57) ABSTRACT

Some embodiments of a medical device anchor system include an anchor device, a tether, and an adapter for securing a medical instrument (such as a catheter or the like) in place relative to a skin penetration point using subcutaneous anchors.

24 Claims, 8 Drawing Sheets

(56) References Cited

U.S. PATENT DOCUMENTS

| | | | |
|---|---|---|---|
| 4,645,492 A | 2/1987 | Weeks | |
| 4,665,906 A | 5/1987 | Jervis | |
| 4,799,495 A | 1/1989 | Hawkins et al. | |
| 4,804,359 A | 2/1989 | Grunwald et al. | |
| 4,813,930 A | 3/1989 | Elliott | |
| 4,936,823 A | 6/1990 | Colvin et al. | |
| 4,986,810 A | 1/1991 | Semrad | |
| 5,041,085 A | 8/1991 | Osborne et al. | |
| 5,067,957 A | 11/1991 | Jervis | |
| 5,122,122 A | 6/1992 | Allgood | |
| 5,190,546 A | 3/1993 | Jervis | |
| 5,256,146 A | 10/1993 | Ensminger et al. | |
| 5,267,960 A | 12/1993 | Hayman et al. | |
| 5,279,564 A | 1/1994 | Taylor | |
| 5,282,794 A * | 2/1994 | Propp | A61M 39/04 604/244 |
| 5,312,337 A | 5/1994 | Flaherty et al. | |
| 5,344,439 A | 9/1994 | Otten | |
| 5,368,017 A | 11/1994 | Sorenson et al. | |
| 5,378,239 A | 1/1995 | Termin et al. | |
| 5,456,671 A | 10/1995 | Bierman | |
| 5,468,230 A * | 11/1995 | Corn | A61M 25/02 604/174 |
| 5,496,277 A | 3/1996 | Termin et al. | |
| 5,578,013 A | 11/1996 | Bierman | |
| 5,597,378 A | 1/1997 | Jervis | |
| 5,599,311 A | 2/1997 | Raulerson | |
| 5,653,718 A | 8/1997 | Yoon | |
| 5,681,288 A | 10/1997 | Schlitt | |
| 5,688,247 A | 11/1997 | Haindl et al. | |
| 5,702,371 A | 12/1997 | Bierman | |
| 5,707,362 A | 1/1998 | Yoon | |
| 5,722,959 A | 3/1998 | Bierman | |
| 5,728,133 A | 3/1998 | Kontos | |
| 5,741,234 A | 4/1998 | Aboul-Hosn | |
| 5,746,720 A | 5/1998 | Stouder, Jr. | |
| 5,755,697 A | 5/1998 | Jones et al. | |
| 5,769,821 A | 6/1998 | Abrahamson et al. | |
| 5,800,402 A | 9/1998 | Bierman | |
| 5,810,781 A | 9/1998 | Bierman | |
| 5,814,065 A | 9/1998 | Diaz | |
| 5,827,230 A | 10/1998 | Bierman | |
| 5,833,664 A | 11/1998 | Seare | |
| 5,833,667 A | 11/1998 | Bierman | |
| 5,857,999 A | 1/1999 | Quick et al. | |
| 5,921,965 A | 7/1999 | Blei | |
| 5,928,266 A | 7/1999 | Kontos | |
| 5,944,732 A | 8/1999 | Raulerson et al. | |
| 5,947,931 A | 9/1999 | Bierman | |
| 5,971,960 A | 10/1999 | Flom et al. | |
| 5,989,265 A | 11/1999 | Bouquet et al. | |
| 6,213,979 B1 | 4/2001 | Bierman | |
| 6,234,999 B1 * | 5/2001 | Wemmert | A61M 5/3243 604/162 |
| 6,290,676 B1 | 9/2001 | Bierman | |
| 6,413,240 B1 | 7/2002 | Bierman et al. | |
| 6,447,485 B2 | 9/2002 | Bierman | |
| 6,540,693 B2 | 4/2003 | Burbank et al. | |
| 6,572,588 B1 | 6/2003 | Bierman et al. | |
| 6,582,388 B1 | 6/2003 | Coleman et al. | |
| 6,582,403 B1 | 6/2003 | Bierman et al. | |
| 6,663,600 B2 | 12/2003 | Bierman et al. | |
| 6,679,851 B2 | 1/2004 | Burbank et al. | |
| 6,695,861 B1 | 2/2004 | Rosenberg et al. | |
| 6,770,055 B2 | 8/2004 | Bierman et al. | |
| 6,896,665 B2 | 5/2005 | Picha et al. | |
| 6,958,044 B2 | 10/2005 | Burbank et al. | |
| 7,056,286 B2 | 6/2006 | Ravenscroft et al. | |
| 8,038,653 B2 | 10/2011 | Rosenberg et al. | |
| 8,235,948 B2 | 8/2012 | Rosenberg et al. | |
| 8,328,764 B2 | 12/2012 | Rosenberg et al. | |
| 2002/0068898 A1 | 6/2002 | McGuckin, Jr. et al. | |
| 2002/0068899 A1 | 6/2002 | McGuckin, Jr. et al. | |
| 2002/0120250 A1 | 8/2002 | Altman | |
| 2002/0165489 A1 | 11/2002 | McGuckin, Jr. et al. | |
| 2003/0083625 A1 | 5/2003 | Bierman | |
| 2005/0043685 A1 | 2/2005 | Schinkel-Fleitmann | |
| 2005/0187578 A1 | 8/2005 | Rosenberg et al. | |
| 2005/0256459 A1 | 11/2005 | Howard et al. | |
| 2006/0079845 A1 | 4/2006 | Howard et al. | |
| 2007/0021685 A1 | 1/2007 | Oepen et al. | |
| 2007/0106330 A1 | 5/2007 | Rosenberg et al. | |
| 2007/0225651 A1 | 9/2007 | Rosenberg et al. | |
| 2007/0232997 A1 | 10/2007 | Glenn | |
| 2008/0140011 A1 | 6/2008 | Hager | |
| 2009/0326470 A1 | 12/2009 | Rosenberg et al. | |
| 2009/0326473 A1 * | 12/2009 | Rosenberg | A61M 25/02 604/180 |
| 2011/0213310 A1 * | 9/2011 | Bierman | A61M 25/02 604/180 |
| 2012/0004617 A1 | 1/2012 | Rosenberg et al. | |
| 2012/0078191 A1 | 3/2012 | Rosenberg et al. | |
| 2013/0072875 A1 | 3/2013 | Rosenberg et al. | |
| 2014/0228810 A1 | 8/2014 | Rosenberg et al. | |
| 2016/0317787 A1 | 11/2016 | Rosenberg et al. | |

FOREIGN PATENT DOCUMENTS

| | | |
|---|---|---|
| WO | WO 2004026152 | 4/2004 |
| WO | WO 2005039419 | 5/2005 |
| WO | WO 2005102438 | 11/2005 |

OTHER PUBLICATIONS

Johnson & Johnson web page printout, "The EndoANCHOR Features and Benefits" printed Sep. 13, 2005, 2 pages.

Johnson & Johnson web page printout, "The EndoANCHOR Firing Sequences" printed Sep. 13, 2005, 2 pages.

Implant Manual. "Interstim Therapy: Model 3093 Lead and Model 3889 Lead." Medtronic, Inc., Minneapolis, MN, 2010, 38 pages.

International Search Report and Written Opinion for PCT/US2014/016042, dated Jun. 3, 2014, 14 pages.

International Preliminary Report on Patentability for PCT/US2014/016042 dated Aug. 27, 2015, 9 pages.

European Search Report in International Application 14/752,197.5, dated Dec. 20, 2016, 5 pages.

* cited by examiner

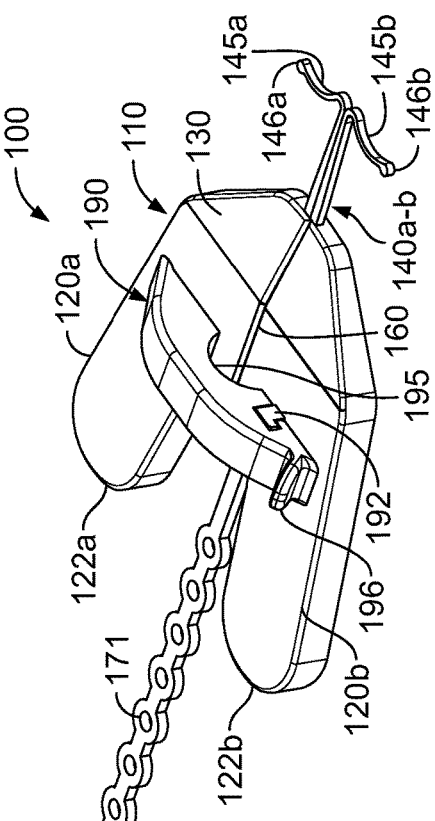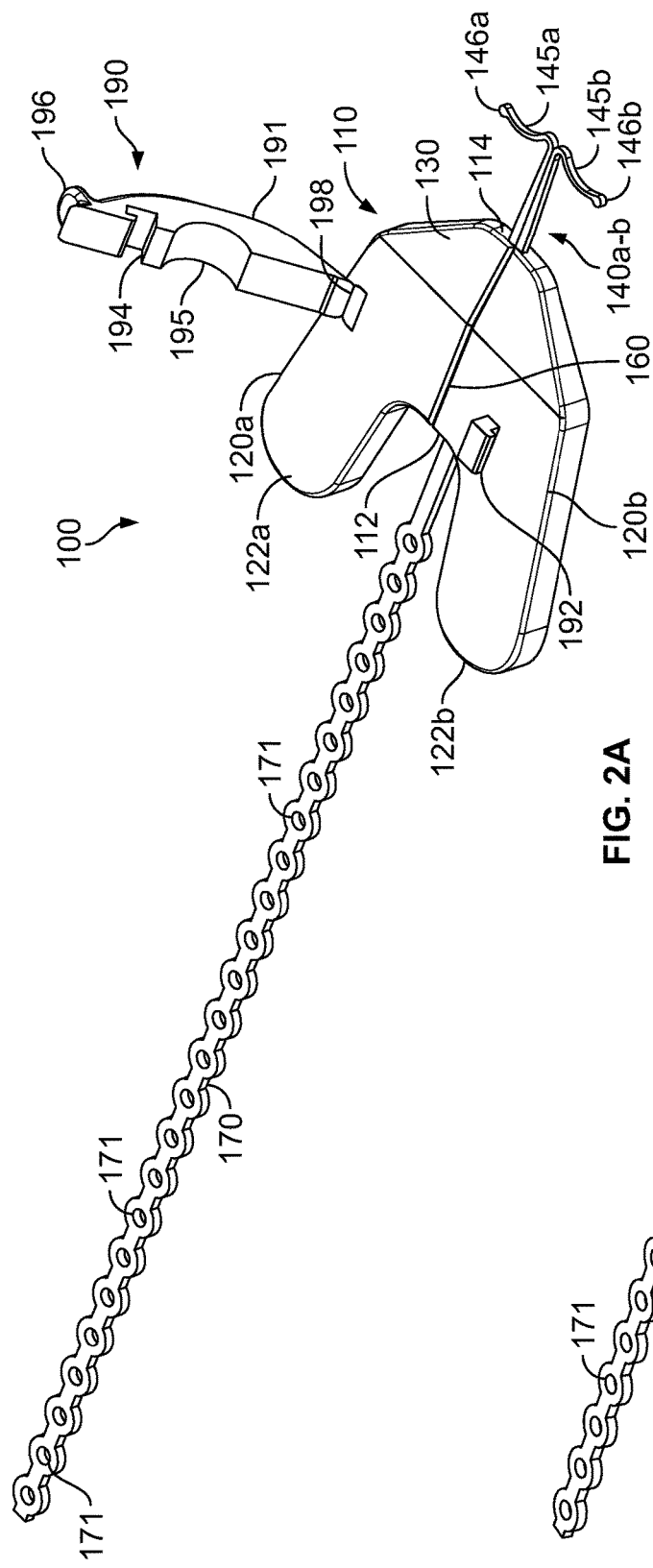

SYSTEMS AND METHODS FOR ANCHORING MEDICAL DEVICES

CLAIM OF PRIORITY

This application is a divisional and claims priority to U.S. patent application Ser. No. 13/766,102, filed on Feb. 13, 2013, the entire contents of which are hereby incorporated by reference.

TECHNICAL FIELD

This document relates to devices, systems, and methods for securing the position of a catheter or another medical instrument, for example, at a skin opening.

BACKGROUND

Venous, arterial, and body fluid catheters are commonly used by physicians. For example, such catheters may be used to gain access to the vascular system for dialysis, for introducing pharmaceutical agents, for nutrition or fluids, for hemodynamic monitoring, and for blood draws. Alternatively, catheters can be used for drainage of fluid collections and to treat infection. Alternatively, catheters can contain electrical leads for neuro-stimulation, cardiac pacing, and the like. Following introduction into the patient, the catheter is secured to the patient. In many instances, the catheter is commonly secured to the patient using an adhesive tape on the skin or by suturing a catheter hub to the patient's skin. In other circumstances, the catheter may be secured to the patient using a subcutaneous anchor mechanism (such as a sleeve or retainer equipped with anchors that are deployed into a subcutaneous region under the skin). In many cases, the medical practitioner will make efforts to clean the skin area around the catheter insertion site for purposes of a patient's comfort, safety, and improved visualization of the catheter insertion site after the catheter is installed.

SUMMARY

Some embodiments of a medical device anchor system are configured to receive a medical instrument (such as a catheter or the like that is optionally equipped with suture wings), and to secure the instrument relative to a skin penetration point. For example, the medical device anchor system can include an anchor device with one or more subcutaneous anchors extending from the base of the anchor device. In some embodiments, the one or more subcutaneous anchors are deployed through the skin penetration point that is already occupied by the catheter, thereby reducing or eliminating the need for installing sutures through the suture wings and the patient's skin. The anchor device can include an attachment feature for coupling a portion of the catheter to the anchor device. The anchor device can also include an attached flexible tether that extends proximally from the base of the anchor device. The flexible tether can be configured to releasably mate with an adapter device of the medical device anchor system. The adapter device can be configured to releasably mate with the catheter, such as the suture wings on a hub of the catheter. When the catheter is secured to the medical device anchor system (at both the anchor device and the tethered adapter), the one or more subcutaneous anchors extending from the anchor device through the skin penetration point reduce or eliminate the need for installing sutures through the suture wings and the patient's skin. Optionally, in some embodiments the anchor device can be adjusted to a folded configuration that aligns the tines of the subcutaneous anchors in a generally side-by-side configuration to facilitate insertion of the one or more subcutaneous anchors through the skin penetration point. Such a configuration may allow the anchor device to be installed after a medical instrument is already in place without the need for a second penetration point for the anchor device. In particular embodiments, the anchor device may be configured to simplify the use of the anchor device, make the anchor device more adaptable to use with medical instruments of different sizes, and to facilitate the maintenance and cleaning of the skin tissue at and around the skin penetration point.

Particular embodiments described herein may include an anchor device for securing the position of a medical instrument. The anchor device may include a first external body comprising a proximal end and a distal end. The anchor device may also include one or more anchors that extend distally from the distal end of the first external body. Each anchor may include a flexible tine that is deployable in a subcutaneous region to secure the first external body relative to a penetration point. The anchor device may further include a tether member that extends proximally from the first external body. The anchor device may also include a second external body that is attachable to the tether member at a position proximally spaced away from the proximal end of the first external body, wherein the second external body is configured to releasably couple to a medical instrument.

In some embodiments, an anchor device for securing the position of a medical instrument may include a retainer body having a proximal end and a distal end. The retainer body can be configured to releasably couple to a first external portion of a medical instrument. The anchor device may also include first and second anchors that extend distally from the distal end of the retainer body. Each anchor may include a flexible tine that is deployable in a subcutaneous region to secure the retainer body relative to a penetration point. The anchor device may further include a tether member configured to extend proximally from the proximal end of the retainer body. The anchor device may also include an adapter that is attachable to the tether at a position proximally spaced a distance away from the retainer body. The adapter can be configured to releasably couple to a second external portion of the medical instrument.

Various embodiments described herein include a method of using a medical anchor system. For example, the method may include deploying subcutaneous anchors of a medical anchor system through a skin penetration point that is occupied by a medical instrument. The subcutaneous anchors may be deployed in a subcutaneous region along an underside of a skin layer proximate to the skin penetration point. Also, the subcutaneous anchors can extend distally from a distal end of a retainer body of the medical anchor system. The method may further include securing a first external portion of the medical instrument to a second body of the medical anchor system. The second body may be tethered to the retainer body via a flexible member that extends proximally away from a proximal end of the retainer body.

These and other embodiments may provide one or more of the following advantages. First, some embodiments of a medical device anchor system can retain a medical instrument in a desired position relative to a skin penetration point without necessarily requiring sutures or skin adhesives. Second, particular embodiments of the medical device anchor system may be readily adaptable to use with catheters or other medical instruments of different sizes, while also securing the catheter or medical instrument to a skin penetration point in a manner that facilitates improved capabilities for inspection and cleaning of the skin tissue at and around the skin penetration point. For example, some embodiments of the medical device anchor system can be equipped with a flexible tether device that secures to the base of an anchor device at one end and to an adapter device at the other end, thereby simplifying temporary movement of the medical instrument relative to the patient's skin (and the skin penetration point), and allowing a practitioner to readily inspect and clean the anchor device and the skin surface near the skin penetration point. Third, in some embodiments, the anchor device may be adjusted between a folded configuration and a non-folded configuration so that the subcutaneous anchors are arranged side-by-side and extend in generally the same direction during both installation through and removal from the skin penetration point. Fourth, in some embodiments, the configuration of the medical device anchor system can simplify the process of installing a medical instrument onto the medical device anchor system. Fifth, in some embodiments, the medical device anchor system can be configured to be usable with a variety of styles and sizes of medical instruments. Sixth, in some embodiments, the medical device anchor system can enable a hub of a catheter or other medical instrument to be disposed in a position that is measurably spaced apart from the skin penetration point (and the anchor device) while still being anchored to the skin penetration point.

The details of one or more embodiments of the invention are set forth in the accompanying drawings and the description below. Other features, objects, and advantages of the invention will be apparent from the description and drawings, and from the claims.

DESCRIPTION OF DRAWINGS

FIGS. 2A-2B are perspective views of an anchor device of the medical device anchor system of FIGS. 1A-1B, in unlatched and latched configurations respectively.

Like reference symbols in the various drawings indicate like elements.

DETAILED DESCRIPTION OF ILLUSTRATIVE EMBODIMENTS

Figures 1A, 1B:
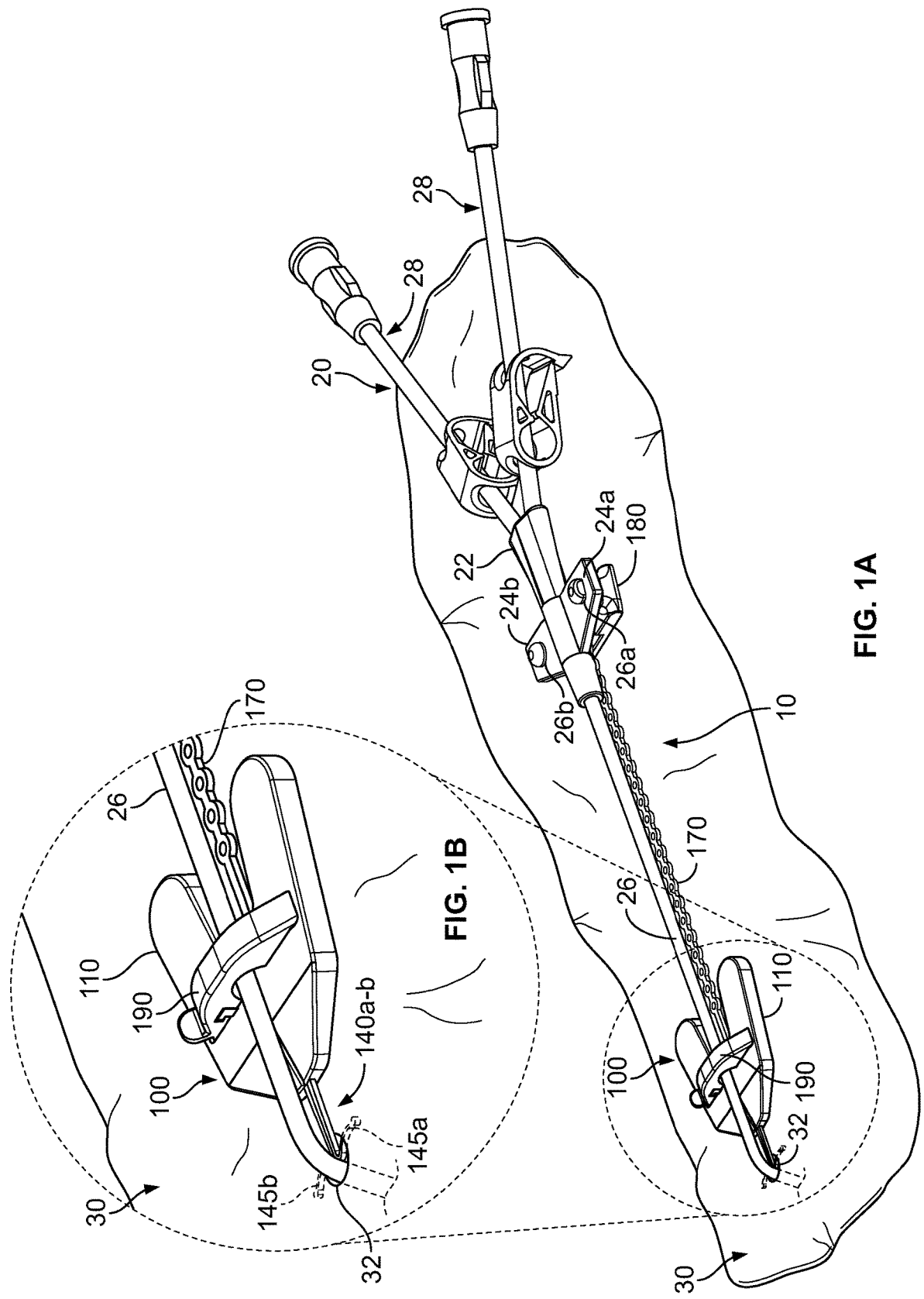
FIGS. 1A-B are perspective views of a medical device anchor system with a portion of the system deployed in a subcutaneous region along an underside of a skin layer, in accordance with some embodiments.

Referring to FIGS. 1A-1B, some embodiments of a medical device anchor system 10 include an anchor device 100, a tether 170, and an adapter 180 for releasably retaining a medical instrument 20 in an operative position relative to a portion of a patient's skin 30. The medical instrument 20 can be mechanically coupled to the medical device anchor system 10 at the anchor device 100 and at the adapter 180. The anchor device 100, in turn, can be coupled to a portion of the skin 30, and the adapter 180 can be coupled to the anchor device 100 via the tether 170. In this manner, the medical device anchor system 10 can act as an intermediary member to retain the medical instrument 20 in a desired position with respect to the skin 30.

In the example embodiment shown in FIGS. 1A-1B, the medical instrument 20 is depicted as a central venous catheter. Hereinafter the medical instrument 20 may alternatively be referred to as "catheter" 20 without limiting the medical instrument 20 to such an embodiment.

In this example, the catheter 20 generally includes a proximal portion 28, a hub 22, and a shaft 26 that extends distally of the hub 22. In use, the shaft 26 of the catheter 20 is inserted through a percutaneous opening formed in the skin (e.g., penetration point 32), and extends distally under the skin 30 (e.g., into a selected body vessel). The distal end of the shaft 26 may be positioned within a vessel to provide vascular access for delivering medications, withdrawing fluids, or providing minimally invasive access into a patient. The hub 22 can interconnect the proximal portion 28 with the shaft 26. In some embodiments, the proximal portion 28 of the catheter 20 may have multiple lumens that extend as isolated internal lumens along an interior of the catheter shaft 26.

Still referring to FIGS. 1A-1B, the medical device anchor system 10 can secure the catheter 20 to the patient using a tethered arrangement. For example, the medical device anchor system 10 can generally include the anchor device 100, the adapter 180, and the tether 170. The tether 170 can mechanically couple the adapter 180 to the anchor device 100 such that the adapter 180 remains spaced apart from the anchor device 100 but tethered thereto. The catheter 20 can be coupled to both the anchor device 100 and to the adapter 180.

In this example, the adapter 180 is located proximally of the anchor device 100. The adapter 180 can be releasably coupled to the anchor device 100 by the elongate flexible tether 170 that extends from the anchor device 100 in a proximal direction. In this example, one end of the tether 170 is fixedly attached to the anchor device 100 and another end is releasably attached to the adapter 180. In some embodiments, the tether 170 is releasably attached to the anchor device 100 and fixedly attached to the adapter 180. In some embodiments, the tether 170 is releasably attached to both the anchor device 100 and the adapter 180. In some embodiments, the tether 170 is fixedly attached to both the anchor device 100 and the adapter 180. Embodiments having one or more releasable attachments can allow the length of the tether 170 between the anchor device 100 and the adapter 180 to be adjustable. That is, in some embodiments the adapter 180 can be positioned at various distances away from the anchor device 100 in accordance with a user's preference.

In some embodiments, the adapter 180 is mechanically coupled to a feature of the catheter 20 such as the hub 22. In particular embodiments, the adapter 180 is configured to mechanically couple with suture wings 24a-b of the hub 22. The coupling of the suture wings 24a-b of the hub 22 to the adapter 180 will be described in more detail below in reference to FIG. 9. In some optional circumstances, the tethered adapter 180 of the medical device anchor system 10 can provide one or more benefits during use. For example, the attachment of the catheter hub 22 to the adapter 180, rather than attachment of the hub 22 directly to the anchor device 100, can facilitate convenient manipulation of the anchor device 100 for cleaning around skin penetration point 32. That is, in some cases the anchor device 100 is manipulated by a clinician or patient while cleaning the skin 30 around the skin penetration point 32. For example, the anchor device 100 may be manipulated to raise it up from the surface of the skin 30 to clean under the anchor device 100. In some embodiments, the catheter 20 is more flexible and more convenient to manipulate at the shaft 26 than at the hub 22. Therefore, the coupling of the shaft 26 to the anchor device 100, rather than the coupling of the hub 22 directly to the anchor device 100, may make cleaning around the skin penetration point 32 more convenient.

In addition to the adapter 180 and tether 170, the medical device anchor system 10 includes the anchor device 100. In this example, the anchor device 100 includes a retainer body 110 and one or more anchors 140a-b that extend distally from a distal end of the retainer body 110. The one or more anchors 140a-b can be configured for deployment through a skin penetration point 32 and into in a subcutaneous layer, so as to releasably retain the anchor device 100 with respect to the skin 30. For example, the retainer body 110 can include a pair of anchors 140a and 140b that extend distally from the retainer body 110 so as to penetrate through the same skin penetration point 32 as the medical instrument 20 while the retainer body 110 remains external to the skin penetration point 32. In some embodiments, the skin penetration point 32 may be defined by a small incision, a puncture, or the like through the dermal layers.

The anchors 140a-b can include subcutaneous tines 145a-b that, after insertion, reside in a subcutaneous region (e.g., a region immediately under the skin 30 that may comprise a fatty tissue layer) so as to secure the position of the anchor device 100—and the catheter 20 retained thereto—relative to the penetration point 32. When the tines 145a-b are deployed in the subcutaneous region 34, the anchor device 100 can be secured to the patient without the retainer body 110 penetrating through the dermal layers of the patient, and without necessarily requiring sutures or adhesive tapes bonded to the skin 30.

As described in more detail below in connection with FIGS. 7-9, the anchor device 100 can be installed into a skin penetration point 32 in accordance with a technique that reduces or eliminates the need to shift the subcutaneous anchors tines 145a-b of the anchors 140a-b to or from a flexed or stressed configuration. As such, the anchor tines 145a-b need not undergo substantial flexing during installation or removal. In these circumstances, the anchors 140a-b may be both installed and removed from the skin penetration point 32 advantageously without the need for an external actuator handle or delivery device to deploy the subcutaneous tines 145a-b.

Still referring to FIGS. 1A-1B, after installation of the subcutaneous anchor tines 145a-b into the subcutaneous layer 34, the retainer body 110 can receive a medical instrument such as catheter 20. Furthermore, optionally, the anchor device 100 can provide a capless design in which the anchor device 100 releasably couples with the shaft 26 of the catheter 20 without the need for attaching a separate cap onto the retainer body 110. For example, the anchor device can be equipped with a latch assembly 190 configured to mate with an exterior portion of the catheter shaft 26 extending distally from the hub 22. As described in more detail below, in some embodiments, the latch assembly 190 is adjustable between an open position and a closed position. In the closed position, the latch assembly 190 can exert a light compression on the exterior of the shaft 26 of the catheter 20, thereby providing a friction fit. On that basis, the shaft 26 of the catheter 20 can be coupled to the anchor device 100, yet the tethered adapter 180 can be arranged to bear an incidental pulling force on the proximal portions 28 of the catheter 20 or the hub 22 of the catheter 20 (thereby reducing the likelihood that the distal shaft 26 would bear such a force).

Figure 3:
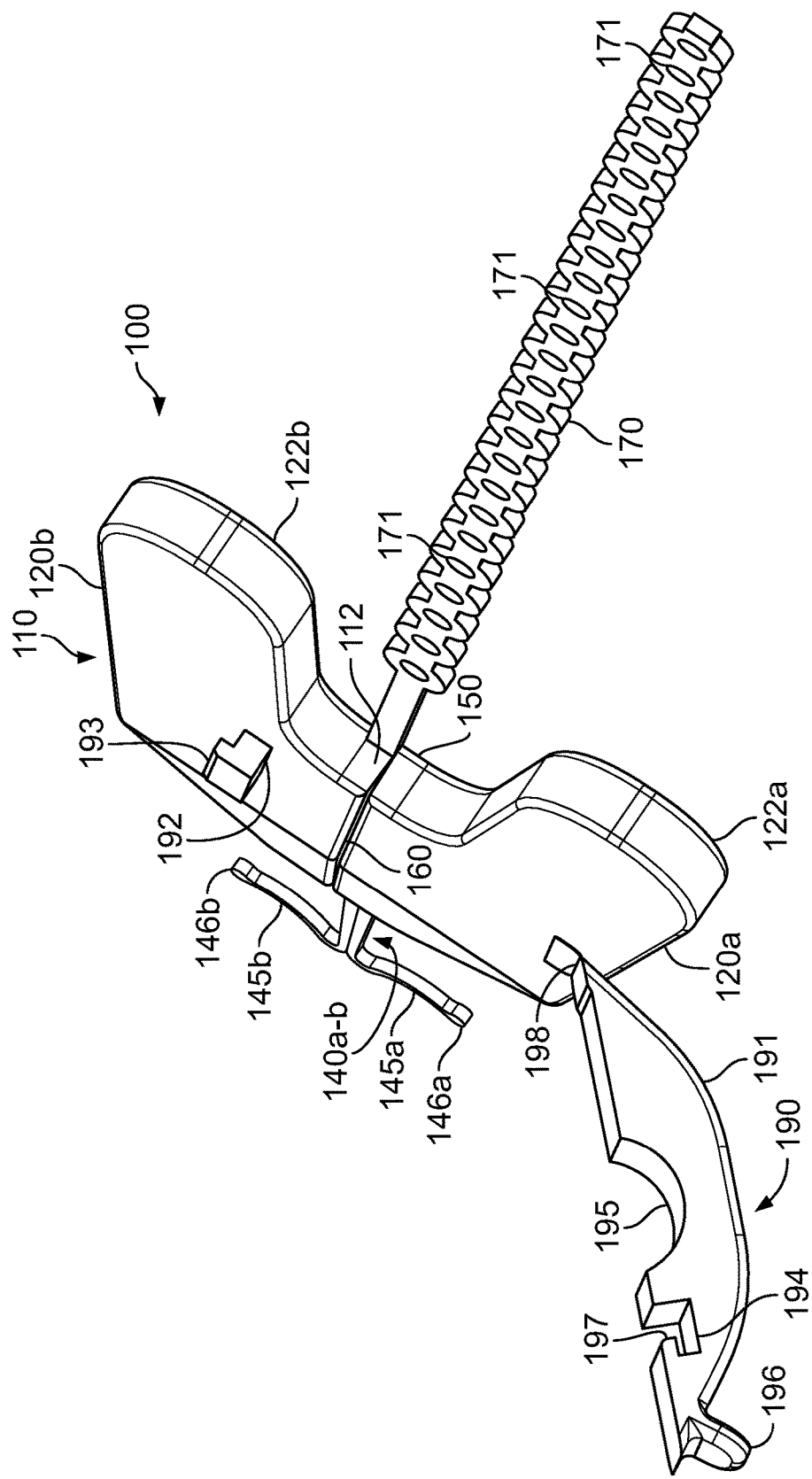
FIG. 3 is another perspective view of an anchor device of the medical device anchor system of FIGS. 1A-1B, in accordance with some embodiments.

Referring now to FIGS. 2A-3, some embodiments of the anchor device 100 can generally include the retainer body 110, the tether 170, and the anchors 140a-b. The tether 170 can be connected to and extend proximally from the proximal end 112 of the retainer body 110. The anchors 140a-b can be connected to and extend distally from the distal end 114 of the retainer body 110. In some embodiments, the anchors 140a and 140b are connected to the retainer body 110 using an over-molding process to secure the anchors 140a-b relative to the retainer body 110. In this embodiment, the retainer body 110 and the anchors 140a and 140b are permanently fixed to one another.

Preferably, at least a portion of each anchor 140a-b comprises a flexible material. In some embodiments, the anchors 140a-b may comprise a material that exhibits superelasticity. In some embodiments, at least a portion of the anchors 140a-b (including the tines 145a-b) may be formed from a length of nitinol wire or from a sheet of nitinol material. Alternatively, the anchors 140a-b may comprise a metal material such as stainless steel (e.g., 304 stainless, 316 stainless, custom 465 stainless, and the like), spring steel, titanium, MP35N, and other cobalt alloys, or the like. In another alternative, the anchors 140a-b may be formed from a resilient polymer material. In some embodiments, the anchors 140a-b can be formed from a material or materials that allow the tines 145a-b to be flexed and can resiliently return to a selected arrangement.

In the embodiment depicted, each of the anchors 140a-b may be designed such that the tines 145a-b have an unstressed position wherein the tines 145a-b have a convex curvature. The convex curvature shape of the tines 145a-b may permit the tines 145a-b to abut against the underside of the dermal layers in a manner that reduces the likelihood of the tine tips 146a-b puncturing the underside of the dermal layers. Preferably, the tine tips 146a-b are rounded bulbs or otherwise non-sharp so as to further protect the underside of the dermal layers. In alternative embodiments, the tines 145a-b may have a generally straight shape that extends substantially perpendicular to the longitudinal shaft portions of the anchors 140a-b to the rounded tips 146a-b.

Figure 6:
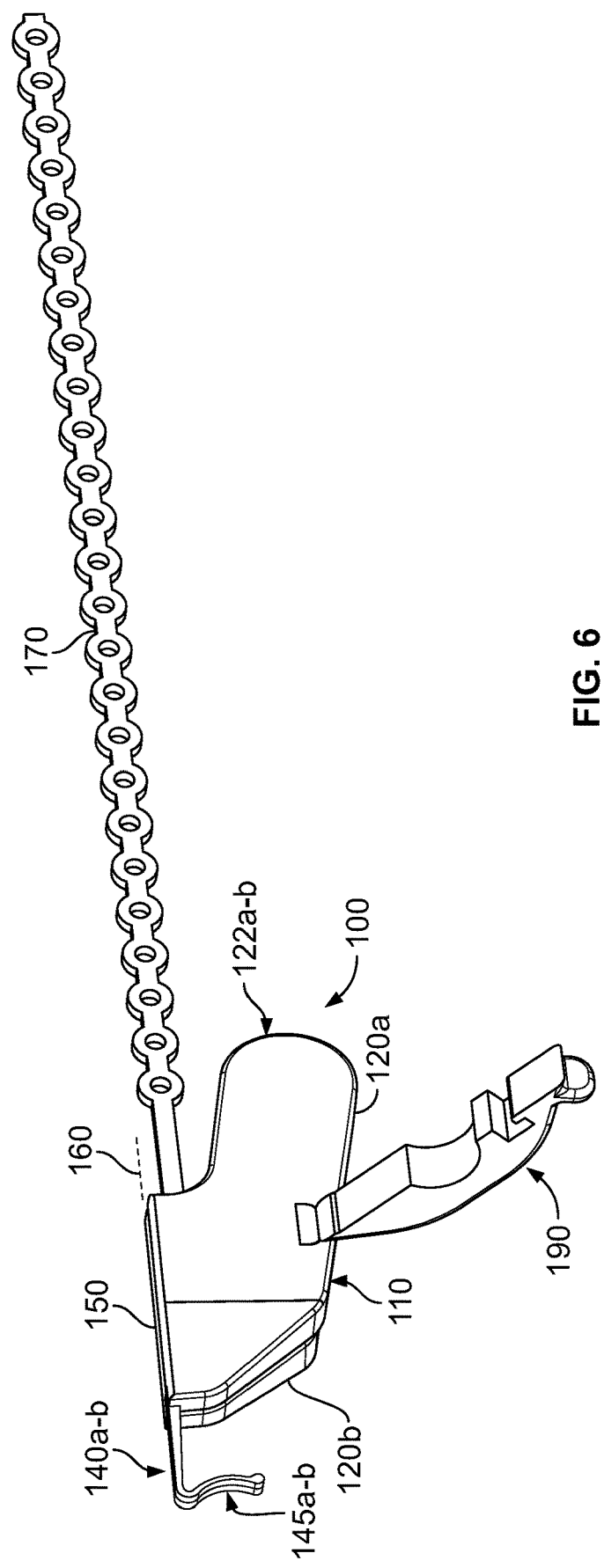
FIG. 6 is a perspective view of an anchor device of the medical device anchor system of FIGS. 1A-1B in a folded condition, in accordance with some embodiments.

Still referring to FIGS. 2A-3, the retainer body 110 can include first and second retainer body portions 120a-b, and a latch assembly 190. The first and second retainer body portions 120a-b can be interconnected by an elastically flexible web portion 150. In particular embodiments, the retainer body 110 is configured to be folded longitudinally about a longitudinal fold axis 160 (e.g., a longitudinally extending region adapted to allowing the retainer body 110 to reversibly reconfigure between a first generally planar position and a second folded position as shown in FIG. 6). In some embodiments, the first and second retainer body portions 120a-b can be substantially mirror images of each other. In alternative embodiments, the first and second portions of the anchor device 100 can be asymmetrical. The first and second retainer body portions 120a-b can include left and right tabs 122*a-b* that can provide convenient grasping locations for folding or otherwise manipulating the retainer body 110.

The retainer body 110 can comprise one or more biocompatible polymer materials (e.g., PVC, polypropylene, polystyrene, or the like). In some embodiments, the retainer body 110 can comprise a combination of such materials. For example, the flexible web portion 150 can comprise an elastically flexible silicone material while the first and second retainer body portions 120*a-b* comprise a less flexible polymer material such as polypropylene, PVC, polystyrene, or the like. In some embodiments, the retainer body 110 can be formed using a molding process in which the retainer body 110 is over-molded around a portion of the anchors 140*a-b*, especially in those embodiments in which the anchors 140*a-b* comprise a metallic material. For example, the left retainer body portion 120*a* can be over-molded around a portion of anchor 140*a* and, during the same or a different molding process, the right body portion 120*b* can be over-molded around a portion of anchor 140*b*. Consequently, as described further below in reference to FIG. 6, when the retainer body 110 is folded, the respective anchors 140*a-b* (being connected to the retainer body portions 120*a-b* respectively) likewise move in conjunction with their respective retainer body portion 120*a-b*.

The flexible web portion 150 of the retainer body 110 can be positioned, for example, generally centrally between the first and second retainer body portions 120*a-b*. The flexible web portion 150 can extend longitudinally from a distal face of the retainer body 110 to a proximal face of the retainer body 110, and can be used to define the fold axis 160 about which the first and second retainer body portions 120*a-b* are pivotable from the non-folded condition to the folded condition (FIG. 6). The left and right retainer body portions 120*a-b* can be connected at opposing sides of the flexible web portion 150. The flexible web portion 150 can comprise an elastically flexible biocompatible polymer material (e.g., silicon, PVC, polypropylene, polystyrene, or the like). In some embodiments, the flexible web portion 150 can be made of the same material as the other portions of the retainer body 110. In other embodiments, the flexible web portion 150 can be made of a different material than the other portions of the retainer body 110. In such a case, the anchor device can be made, for example, using an insert molding operation. The flexible web portion 150 can be biased to resiliently maintain the non-folded shape of the anchor device 100 as depicted in FIGS. 2A-3. When the anchor device 100 is folded along the fold axis 160 due to a user's grasp (refer, for example to FIG. 7), the flexible web portion 150 can undergo elastic deformation such that the flexible web portion 150 biases the anchor device 100 to return the non-folded condition upon release by the user.

The retainer body 110 in this embodiment further includes the first and second tabs 122*a-b*, are configured to enable a user to readily manipulate and fold the retainer body 110 about the fold axis 160 defined by the flexible web portion 150. For example, as described further in reference to FIGS. 6 and 7, the user can pinch the first and second tabs 122*a-b* to induce a pivoting motion of the first and second retainer body portions 120*a-b* toward one another (e.g., pivoting about the fold axis 160). The first and second tabs 122*a-b* are also configured to provide a U-shaped cutout region 165 between the first and second tabs 122*a-b*. This u-shaped cutout region 165 can more readily provide visualization and access to the skin region under the retainer body 110 for inspection and cleaning of the skin 30 around the skin penetration point 32.

Still referring to FIGS. 2A-3, in some embodiments, the retainer body 110 has a sloped nose region 130. The sloped nose region 130 can be a generally planar surface near the distal end of the retainer body 110 that is oriented at a different angle than the generally planar surfaces of the first and second retainer body portions 120*a-b*. The sloped nose region 130 can decline from the generally planar surfaces of the first and second retainer body portions 120*a-b* such that the nose region 130 slopes downward in a distal direction toward the longitudinal shafts of the anchors 140*a-b* (e.g., and thus downward to the skin penetration point 32 when the anchor tines 145*a-b* are deployed). The sloped nose region 130 can facilitate an orientation of the shaft 26 of the catheter 20 that is directed toward the skin penetration point 32. In this manner, the stresses that may potentially be exerted on the skin 30 proximal to the skin penetration point 32 by the shaft 26 of the catheter 20 can be reduced.

As previously described, the retainer body 110 in this embodiment includes the latch assembly 190, which can include a hinged portion 191 and a mating engagement feature 192. In some embodiments, the hinged portion 191 is attached to a particular retainer body portion, and the engagement feature 192 is attached to the other retainer body portion. For example, the illustrated embodiment has the hinged portion 191 attached to the left body portion 120*a*, and the engagement feature 192 attached to the right body portion 120*b*. As such, when the hinged portion 191 is mated with the engagement feature 192, the latch assembly 190 can resist the aforementioned folding motion about the fold axis 160. In some embodiments, the positions of the hinged portion 191 and the engagement feature 192, in relation to the first and second retainer body portions 120 *a-b*, can be reversed in comparison to the illustrated arrangement.

The latch assembly 190 can be adjusted between an open configuration (illustrated in FIGS. 2A and 3) and a closed configuration (illustrated in FIG. 2B). As described further in reference to FIGS. 8 and 9, the anchor device 100 can receive the shaft 26 of the catheter 20 when the latch assembly 190 is arranged in the opened configuration. The hinged portion 191 can then be pivoted to the closed configuration, and latched to the engagement feature 192 to mechanically couple the shaft of the catheter 20 to the anchor device 100. Accordingly, the latch assembly 190 can transition between the open configuration and the closed configuration by manually pivoting the hinged portion 191. The hinged portion 191 can include a tab 196 that provides a convenient way of grasping onto or manipulating the position of the hinged portion 191. The hinged portion 191 can be attached to the retainer body 110 by a hinge 198. The hinged portion 191 can pivot about the hinge 198.

In some embodiments, the hinge 198 of the hinged portion can be formed as a living hinge. That is, the hinged portion 191 can be molded integrally with the retainer body 110. The integrally molded hinged portion 191 can be attached to the retainer body 110 by a thin web of material that is flexible and resilient enough to perform as the hinge 198. In some embodiments, the hinged portion 191, hinge 198, engagement feature 192, and retainer body 110 can be made from the same material (e.g., the materials described above in relation to the retainer body 110). In some embodiments, a variety of dissimilar materials can be used for the various components. In some embodiments, an insert molding process can be used to accommodate the use of a variety of dissimilar materials for the various components. For example, in some embodiments a flexible silicone can be used for the hinge 198 and/or the hinged portion 191, while a more rigid material can be used for other portions of the retainer body 110. In some embodiments, other suitable types of hinge mechanisms (other than a living hinge) can be used. For example, in some embodiments a pin and collar arrangement can be used.

While the hinge 198 and hinge portion 191 are attached to one of the retainer body portions, the engagement feature 192 resides on the other retainer body portion. In some embodiments, the engagement feature 192 is integrally molded as a part of its respective retainer body portion. In some embodiments, the engagement feature 192 is mechanically attached to the retainer body 110 after the formation of the retainer body 110.

In the closed configuration (FIG. 2B), the hinged portion 191 is coupled to the engagement feature 192 to releasably latch the hinged portion 191 to the engagement feature 192. In some embodiments, the hinged portion 191 includes a receptacle 194 that is complimentarily shaped in relation to the engagement feature 192. That is, the receptacle 194 can be shaped to physically mate with, or snap onto, the engagement feature 192. A variety of suitable mechanical designs and techniques can be used to latch the hinged portion 191 in the closed configuration. For example, the hinged portion 191 of the illustrated embodiment (as best seen in FIG. 3) includes a receptacle 194 with a lip 197 that gets positioned behind a protrusion 193 of the engagement feature 192 to latch the hinged portion 191 in the closed configuration. The materials comprising the walls of the receptacle 194 and/or the engagement feature 192 can be made elastic enough to enable them to be deformed or stretched during the engagement process. In some alternative embodiments, the hinged portion 191 includes a barbed protrusion that projects into a complimentary recess in the opposite retainer body portion when the hinged portion 191 is pivoted to its closed configuration. The hinged portion 191 can be latched in the closed configuration and unlatched to the open configuration. That is, the latching of the latch assembly 190 is reversible.

In some embodiments, the latch assembly 190 in the closed configuration also prevents the retainer body 110 from inadvertently folding. As best seen in FIG. 2B, the latched hinged portion 190 can serve as a supplemental stabilizer to the restrain the first and second retainer body portions 120a-b from pivoting or folding (about the fold axis 160) in relation to each other. Such a feature can be beneficial for maintaining the medical device anchor system 10 in a proper operative orientation with respect to the patient.

In some embodiments, the hinged portion 191 also includes a clearance area 195. The clearance area 195 can be configured to accommodate a portion of the medical instrument, such as the shaft 26 of the catheter 20. In some embodiments, the clearance area 195 is sized and shaped to create light interference fit with the shaft 26. That is, when the hinged portion 191 is latched in the closed configuration, the surface of the clearance area 195 can exert a light force on the outside of the shaft 26 to couple the shaft 26 to the anchor device 100. In some embodiments, the wall of the clearance area 195 includes a surface layer or discrete portions of soft durometer material or high friction material, (e.g., silicon and the like) that contacts and grips the medical instrument 20. In some embodiments, the surface of the clearance area 195 includes lateral ridges or a knurled surface to enhance the friction grip of the hinged portion 191 on the shaft 26.

Still referring to FIGS. 2A-3, the elongate flexible tether 170 can extend in the proximal direction away from the anchor device 100. As will be described further in reference to FIG. 4, the tether 170 can interconnect the anchor device 100 and the adapter 180 and can be configured to transfer tensile forces from the adapter 180 to the anchor device 100 (which is anchored to the skin penetration point). Therefore, one end of the tether 170 is attached to the anchor device 100, and another end or portion of the tether 170 is attached to the adapter 180. As described previously, the tether 170 can be releasably or fixedly attached to the anchor device 100 and the adapter 180. In the illustrated embodiment, the tether 170 is fixedly attached to the anchor device 100 and releasably attached to the adapter 180.

The tether 170 of the example embodiment is attached to the proximal end of the retainer body 110 (refer, for example, to FIG. 3). In some embodiments, the tether 170 is integrally molded with the retainer body 110. In some embodiments, the tether 170 is initially a separate part that is later insert molded with the retainer body 110. In some embodiments, the tether 170 is a separate part that is mechanically mounted or bonded to the retainer body 110 after the formation of the retainer body 110. In some embodiments, the tether 170 can be attached to a particular retainer body portion, e.g., the first or second retainer body portion 120a or 120b (e.g., offset from the flexible web portion 150 to avoid interfering with the aforementioned folding motion about the fold axis 160). For example, in the illustrated embodiment the tether 170 is attached to the right retainer body portion 120b. In some embodiments, the tether 170 is attached to the left retainer body portion 120a. In some embodiments, the tether 170 is attached to the retainer body 110 near the fold line 160. In some embodiments, the tether 170 can be attached to the elastically flexible web portion 150. In some embodiments, the tether 170 can be integrally molded with the elastically flexible web portion 150.

The tether 170 can have a length suitable to maintain the adapter 180 (and the attached catheter hub 22) slightly spaced apart from the anchor device 100. For example, the tether 170 can be in the range of about 1 cm to about 10 cm in length, about 2 cm to about 6 cm in length, and about 5 cm in length for the particular embodiment depicted in FIG. 3. Also, the tether 170 can comprise a biocompatible polymer material, such as polyurethane, PVC, silicone, polypropylene, and polystyrene, to name a few examples.

As previously described, the tether 170 can be releasably attachable to the adapter 180 at one of a number of positions so that a user can select a particular spacing between the adapter 180 and the retainer body 110. In some embodiments, the adapter 180 can be spaced apart from the anchor device in the proximal direction by a distance of at least about 1 cm, about 2 cm to about 10 cm, and about 3 cm to about 5 cm. In the depicted embodiment, a portion of the tether 170 can include a series of holes 171. The holes 171 can be used to mating with corresponding stanchions extending from the adapter 180, thereby providing a releasable coupling between the tether 170 and the adapter 180.

Figure 4:
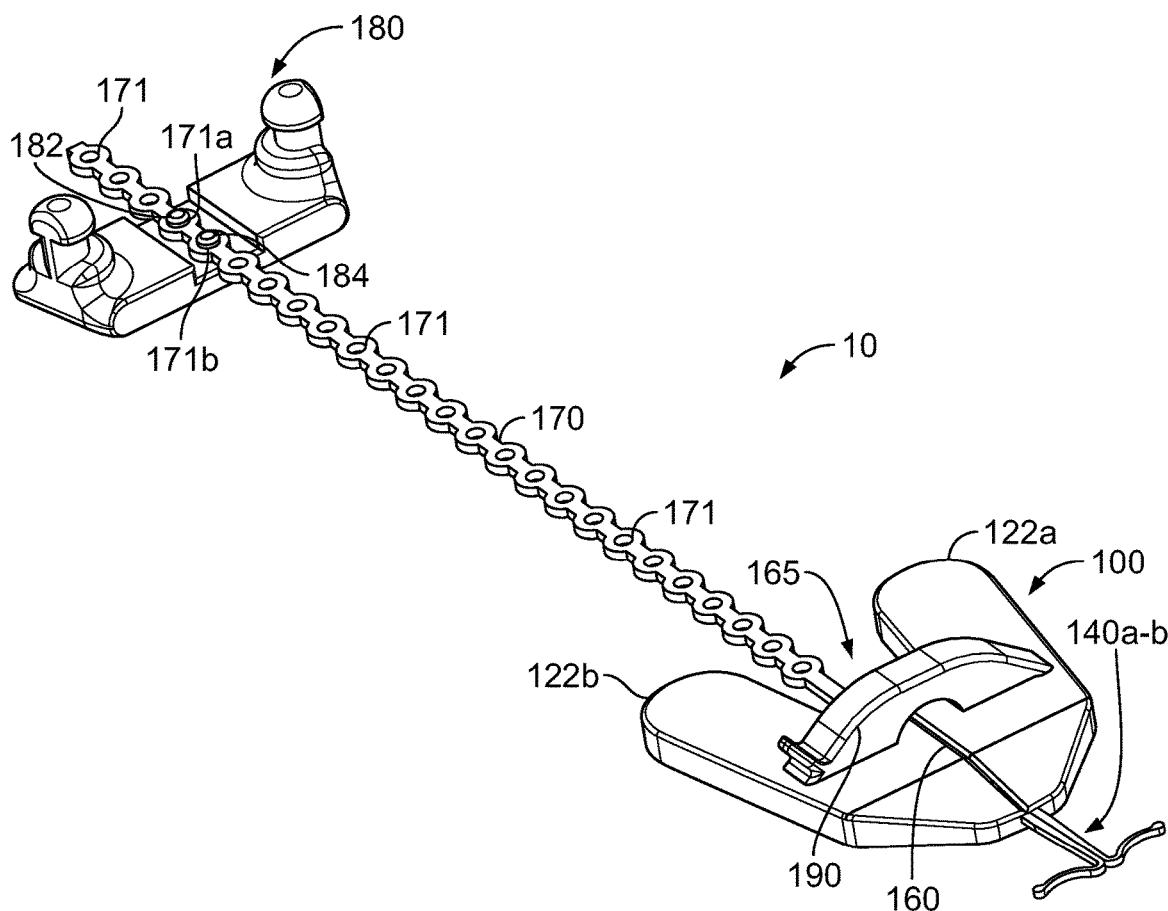
FIG. 4 is a perspective view of the medical device anchor system of FIGS. 1A-1B for use in securing the position of a medical instrument.
Figure 5:
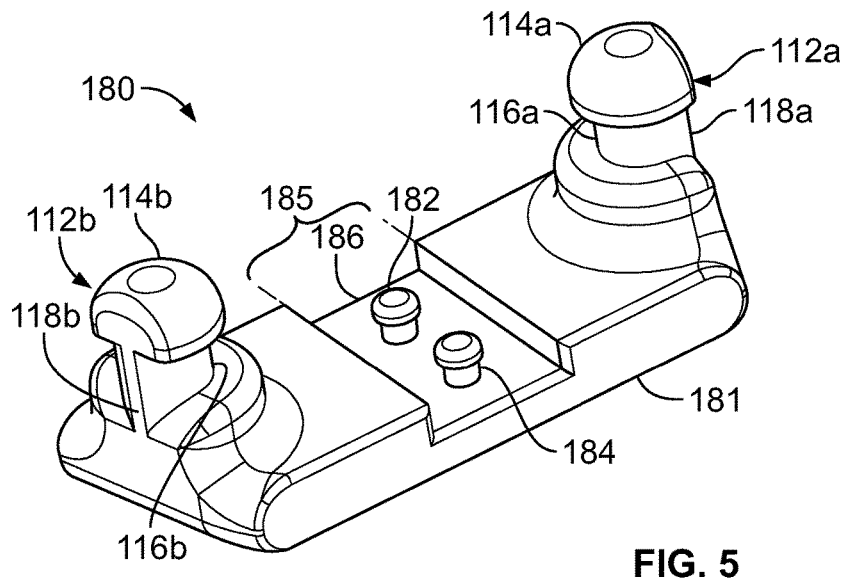
FIG. 5 is a perspective view of an adapter device of the medical device anchor system of FIGS. 1A-1B, for releasably engaging with a medical instrument.

Referring now to FIGS. 4-5, the adapter can be releasably coupled to the tether 170 at a selected location so that the adapter 180 is spaced away in a proximal direction from the proximal end of the anchor device 100. In this embodiment, the adapter 180 includes a base 181, a tether engagement region 185, and retention posts 112a-b. The retention posts 112a-b are example features for coupling with the aforementioned medical instrument, such as the hub 22 of the catheter 20. The tether engagement region 185 exemplifies features for coupling with a tether, such as the example tether 170. The base 181 is a structural member of the adapter 180.

In some embodiments, the adapter 180 is injection molded as a single unitary part. In some embodiments, the adapter 180 is machined or otherwise formed. In some embodiments, the adapter 180 is assembled from separate components. In particular embodiments, the components of the adapter 180 can be made from similar, or dissimilar materials. In some embodiments, the components of the adapter 180 can comprise one or more biocompatible polymer materials (e.g., PVC, polypropylene, polystyrene, silicone or the like).

As shown in FIG. 5, the tether engagement region 185 of the depicted adapter 180 includes features such as a recess 186 and engagement stanchions 182 and 184. The recess 186 can act as a channel to receive the tether 170 therein. The engagement stanchions 182 and 184 are configured to mate with selected holes 171 of the tether 170. In some embodiments, the engagement stanchions 182 and 184 are mushroom-shaped. That is, the free ends of the engagement stanchions 182 and 184 have a bulbous shape that is supported by an under-cut cylindrical base portion with a smaller diameter. In other embodiments of the medical device anchor system 10, the adapter can employ other mechanisms for coupling with the tether 170. For example, in some embodiments the adapter 180 can include a sleeve for receiving the tether 170. The sleeve can include a pawl-like member that is biased to engage with and lock to the holes of the tether 170. The pawl-like member can be manually displaced to temporarily unlock it from the tether during the coupling of the tether to the adapter, or during adjustment of the operative length of the tether.

Referring again to FIGS. 4-5, the adapter 180 can be releasably coupled to the tether 170 by engaging two of the holes 171 with the engagement stanchions 182 and 184. In general, the tether 170 can be resiliently deformed when the two selected holes 171 are urge into engagement with the 182 and 184. The bulbous free ends of the engagement stanchions 182 and 184 can cause the tether 170 to be releasably detained on the adapter 180. For example, a first hole 171a can be coupled to engagement stanchion 182 and a second hole 171b can be coupled to engagement stanchion 184. Because the tether 170 includes a series of holes 171, the operative length of the tether is adjustable. That is, the distance between the anchor device 100 and the adapter 180 is affected by which holes 171 the engagement stanchions 182 and 184 are coupled to, and any set of two neighboring holes 171 can be selected by the user. If, the user elects to secure the adapter 180 to an intermediate set of holes 171 such that an excess length of the tether 170 extends proximally away from the adapter (e.g., an "unused" portion of the tether 170 in some circumstances), the excess length of the tether 170 can be trimmed off. Such a trimming operation can occur either before or after the adapter 180 is secured to the selected set of holes 171 of the tether 170. Furthermore, such a trimming operation can occur either before or after the catheter 20 is secured to the adapter 180 (as described below).

The retention posts 112a-b of the adapter 180 can be configured to provide a releasable coupling interface with the catheter 20 or other medical instrument while also providing features that simplify the overall use of the medical device anchor system 10. For example, in this embodiment, the retention posts 112a-b may provide the user with a simplified coupling technique for mating the adapter 180 to the catheter 20, and may furthermore do so without the need for an attachable cap device or skin sutures.

Figure 9:
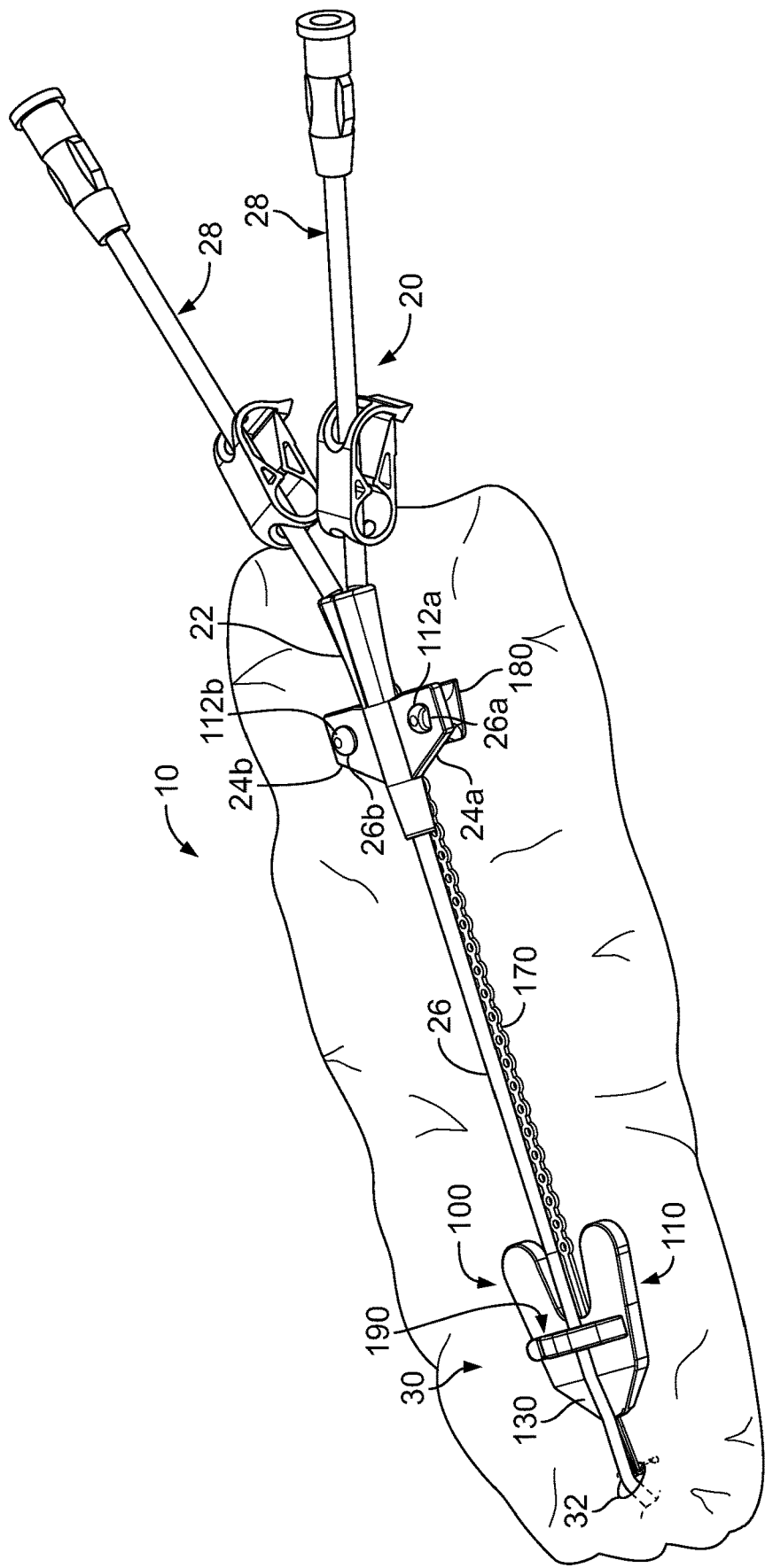

In the depicted example, the retention posts 112a-b are sized and spaced apart in a manner that is configured, for example, to be coupled with apertures 26a-b located on the wings 24a-b of the hub 22 of a catheter 20 (refer to FIGS. 1 and 9). In this embodiment, the retention posts are substantially equally spaced from the center point of the adapter 180. The retention posts 112a-b can include generally mushroom-shaped heads 114a-b, stem portions 116a-b, and relief portions 118a-b. In such circumstances, each of the retention posts 112a-b may have a generally asymmetric shape about a vertical plane extending through a central vertical axis of each respective retention post 112a-b and extending generally parallel to an axis defined by the engagement stanchions 182 and 184.

The shape and position of the retention posts 112a-b can permit a practitioner to intuitively mate the wings 24a-b of the catheter 20 (FIGS. 1A-1B) with the adapter 180, and optionally, without the need for secondary locking mechanisms such a separate cap device that attaches to the adapter 180 or anchor device 100. The mushroom-shaped heads 114a-b can have rounded tops that help the user align the apertures 26a-b with their respective retention posts 112a-b. In some embodiments, the mushroom-shaped heads 114a-b can be sized to have a low interference fit with the apertures 26a-b. For example, if the hub 22 of the medical device 20 comprises a flexible material, the user can readily urge the hub 22 into a mating engagement with the retention posts 112a-b of the adapter 180 by forcibly advancing the apertures 26a-b over the mushroom-shaped heads 114a-b. Thus, when securing the medical device 20 to the adapter 180, the user can align the apertures 26a-b with the mushroom-shaped heads 114a-b and lightly press the hub 22 of the medical device 20 against the adapter 180 so that the apertures 26a-b pass over and below the mushroom-shaped heads 114a-b. The hub 22 can be pressed onto the adapter 180 by engaging one side at a time or by engaging both sides simultaneously. At that stage, the apertures 26a-b have passed over the mushroom-shaped heads 114a-b and surround the stem portions 116a-b of the retention posts 112a-b, thereby releasably securing the hub 22 of the medical instrument 20 onto the adapter 180.

When the medical instrument 20 is installed on the adapter 180, the apertures 26a-b are engaged with the stem portions 116a-b of the adapter 180. The relative diameters of the apertures 26a-b and the stem portions 116a-b can advantageously provide for a slightly snug fit between the apertures 26a-b and the stem portions 116a-b. Such a snug fit can reduce the collection of contaminant materials between the apertures 26a-b and the stem portions 116a-b.

The retention posts 112a-b can optionally include the aforementioned relief portions 118a-b. The relief portions 118a-b are generally planar or slightly curved surfaces on the sides of the retention posts 112a-b that act as material relief areas to make it easier to remove the wings 24a-b from retention posts 112a-b. In other words, the relief portions 118a-b can facilitate removal of the medical instrument 20 from the adapter 180. Specifically, the relief portions 118a-b can allow the user to slide their finger along the side of the adapter 180, to better grasp the wings 24a-b between their thumb and forefinger, and to thereafter "peel" the wings 24a-b off the retention posts 112a-b. In some circumstances, the relief portions 118a-b can similarly facilitate the act of securing the wings 24a-b over the retention posts 112a-b.

Some alternative embodiments of the adapter 180 include retention posts that can be positionally adjusted relative to the base 181. For example, the adjustable retention posts can be selectively mounted at different positions relative to the base 181, which can provide the capability for the user to select different dimensional distances between the retention posts. This feature can enable the adapter 180 to mate with a wider variety of medical instruments. That is, in some embodiments, the positions of the retention posts can be adjustable to accommodate coupling with a variety of medical instruments that have different sized mounting features (e.g., such as different catheters having differently shaped hubs/wings). For example, certain catheter hubs may have mounting features that have a different dimensional spacing in comparison to other catheter hubs. This feature can also simplify the user's selection of anchor devices. In other words, since one adapter can be adjusted to accommodate a wider range of medical instruments, a single adapter can be selected and configured in accordance with the mounting features of the medical instrument immediately before deployment.

Some further alternative embodiments of an adapter 180 can be equipped with retention members (other than posts) that are flexible and therefore movable with respect to the base 181. Such flexibility of the retention members can enable the adapter 180 to couple with any of a variety of medical instruments having a different of mounting interfaces. For example, while some medical instruments include wings with apertures, other medical instruments may be configured with a different type of mounting interface. Providing an adapter 180 with flexible retention members can enable the medical device anchor system 10 to thereby couple with a wider variety of medical instruments. This feature can permit simplified user selection of anchor device systems by providing a adapter 180 that is adaptable to a wider variety of medical instruments.

For example, in some embodiments, the flexible retention members can comprise flexible binding straps having a structure somewhat similar to cable ties. The flexible retention members can be fixedly attached to the base 181 of the adapter 180, for example by insert molding, welding, gluing, clamping, and so on. The elongate flexible portions of the flexible retention members can be used to capture and secure the medical instrument 20. For example, in some embodiments the flexible retention members can be routed through apertures located in the wings of a catheter hub. In other embodiments, the flexible retention members can be routed so as to capture the medical instrument in other manners— such as by routing the flexible retention members over flanges or other outer surfaces, across outer surfaces in an "x" pattern, over individual tubes of a multi-tube device, and so on. When the flexible retention members are engaged with the medical instrument, the flexible retention members can be firmly locked in place using receiver locking devices that are fixedly attached to the adapter 180. In some embodiments, the receiver locking device can be a ratchet-type receiver mechanism that locks with a tooth surface along the side of the corresponding flexible retention member. Such a configuration can allow the flexible retention members to be pulled through the ratchet-type receiver mechanism in one direction, which thereby locks the flexible retention members tightly in place until the medical instrument 20 is released at the end of the procedure by unlocking or severing the retention members.

Referring now to FIG. 6, in this example embodiment, the anchor device 100 may include features that allow the individual anchors 140a-b to be moved relative to one another so as to facilitate both insertion and removal of the anchor device 100 through the skin penetration point 32. For example, the anchor device 100 may have a foldable configuration in which a first portion 120a of the retainer body 110 is pivotably coupled via a flexible hinge portion 150 to a second portion 120b of the retainer body 110. As shown, the latch assembly 190 is in its open or unlatched configuration while the anchor device 100 is folded or being folded.

More specifically, in this embodiment, the first retainer body portion 120a and the second retainer body portion 120b can be flexibly pivoted with respect to each other along a fold axis 160 extending longitudinally through the retainer body 110. To initiate the folding process of the anchor device 100, the user can apply a bending moment about the fold axis 160 to the first and second tabs 122a-b of the anchor device. Such a bending moment can cause an elastic deformation of the flexible web portion 150 so as to fold the anchor device along the fold axis 160. The first retainer body portion 120a can be fixedly coupled to the anchor 140a, and the second retainer body portion 120b can be fixedly coupled to the anchor 140b. Thus, as shown in FIG. 6 (and also in FIG. 7), when the first and second retainer body portions 120a-b are pivoted about the fold axis 160, the two anchors 140a-b likewise pivot relative to one another. This process of pivoting can cause the anchor device to transition from a non-folded condition (shown in FIGS. 2A-3 and in FIGS. 1A-1B) in which the tines 145a-b extend generally away from one another to a folded condition (shown in FIGS. 6 and 7), in which the tines 145a-b are generally adjacent to each other and oriented to extend in substantially the same direction. Similarly, when the bending moment from the user is released, the anchor device can be biased to return the anchor device 100 from the folded condition to the non-folded condition. In the depicted embodiment, the tines 145a-b can be rotated about 75-degrees to about 105-degrees, and preferably about 90-degrees, during the transition between the non-folded condition and the folded condition. The anchor device 100 can be arranged in the folded condition during both insertion and removal of the subcutaneous tines 145a-b so as to reduce the likelihood of the tines 145a-b causing damage to the skin 30.

Figure 7:
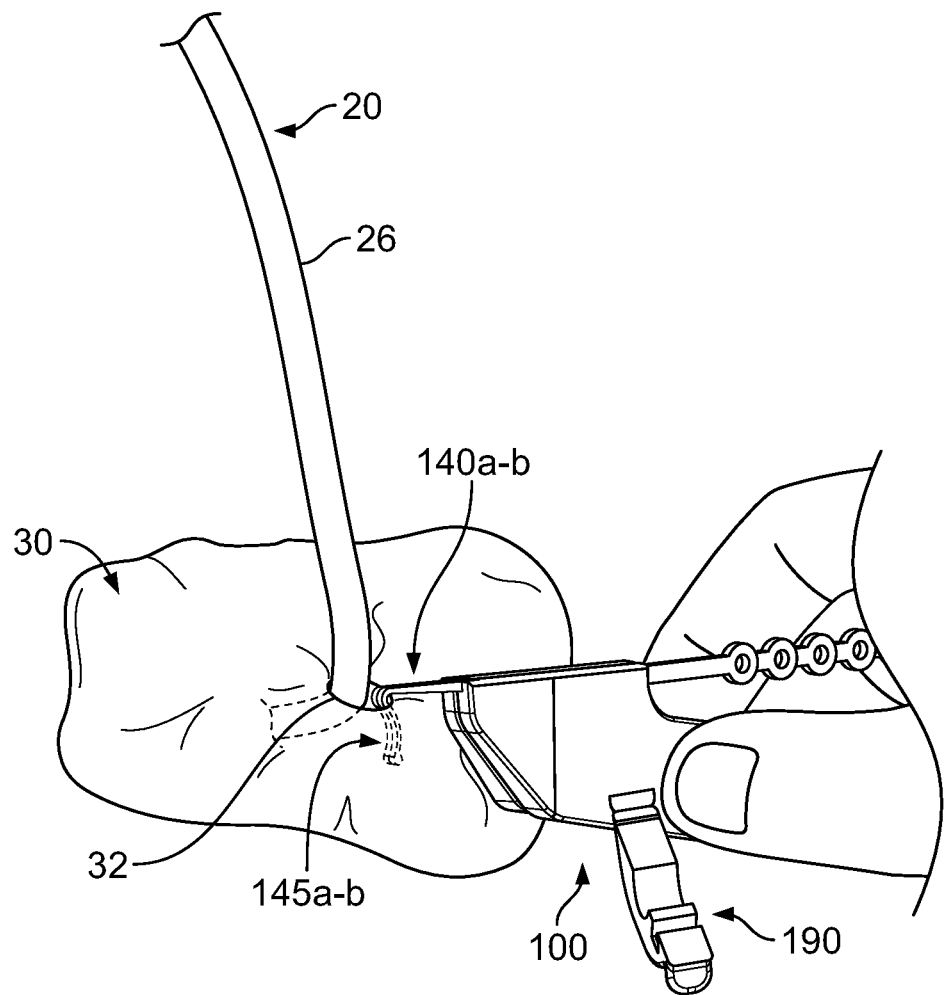
FIGS. 7-9 are perspective views depicting an example process for deploying the medical device anchor system of FIGS. 1A-1B, including securing a medical instrument onto the medical device anchor system.
Figure 8:
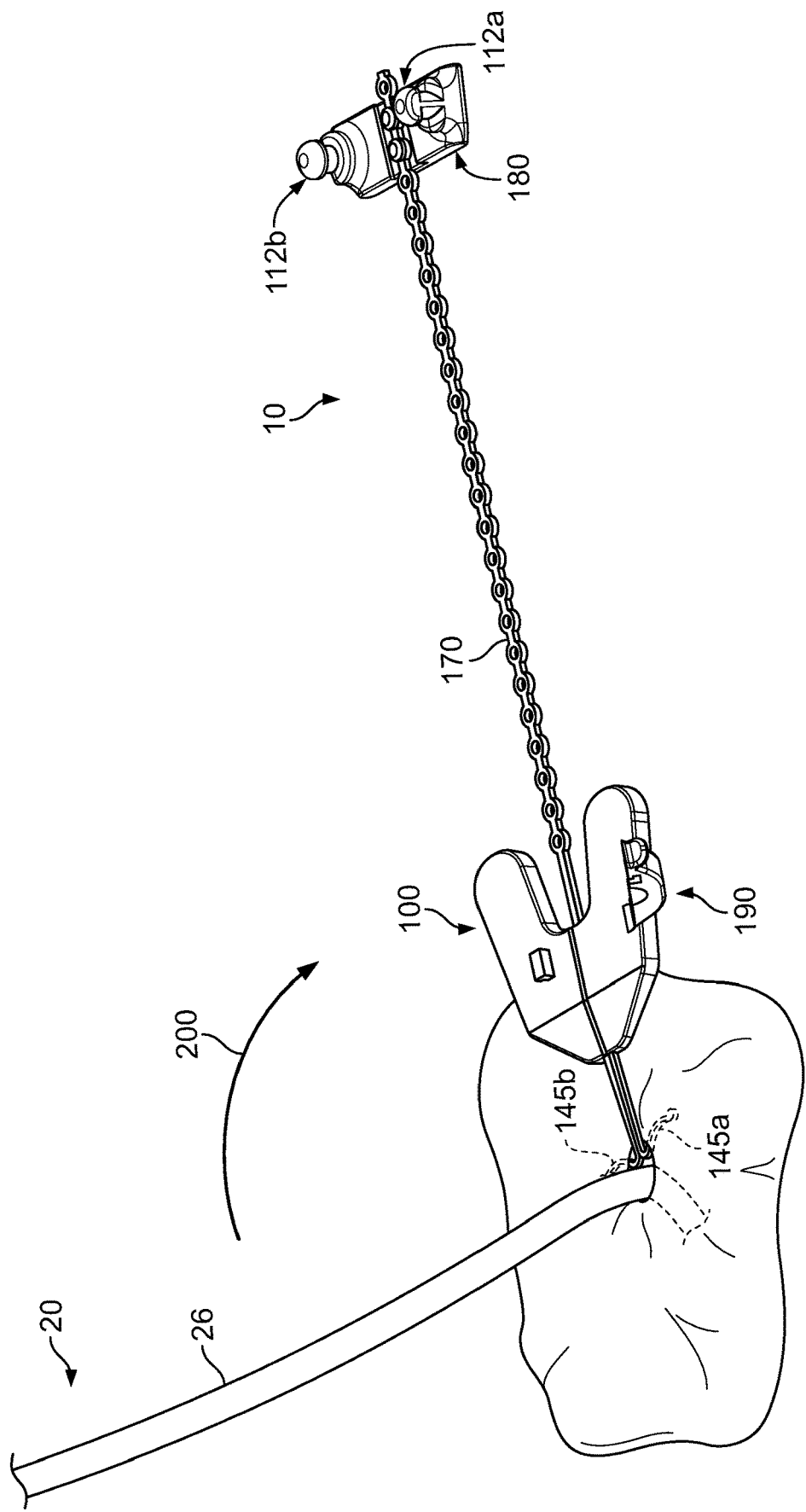

Referring now to FIGS. 7-9, some implementations of a process for using the system 10 can provide a convenient and flexible securement of the medical instrument 20 to the skin penetration point 32. In such implementations, the anchor system 10 can deploy the anchors 140a-b through the same skin penetration point 32 as the medical instrument 20, and furthermore, the anchor system can then releasably retain an external portion of the medical instrument 20 during the duration of a medical procedure. In the illustrated example, the medical instrument is a central venous catheter 20 that is inserted into a percutaneous opening surgically formed in the skin (e.g., penetration point 32) and into a vessel to provide vascular access for delivering medications or minimally invasive devices into a patient. As shown in FIG. 7, after placement of the catheter 20 through the penetration point 32 of the skin 30, the user can grasp the anchor device 100 in the folded condition and deliver the anchors 140a-b toward the penetration point 32 such that the free ends of the tines 145a-b are contemporaneously inserted through the penetration point 32 while the tines 145a-b are in a generally side-by-side condition. In particular embodiments, the subcutaneous tines 145a-b are inserted through the skin penetration point 32 while the user conveniently grasps the tabs 122a-b (FIG. 6) of the retainer body 110 of the anchor device 100 and applies an insertion force until the convexly curved body portions of the subcutaneous tines 145*a-b* are positioned below the surface of the skin 30 (while the remainder of the anchor device 100 resides external to the skin 30).

As the anchor device 100 is inserted through the penetration point 32, the tines 145*a-b* may be maintained in the generally side-by-side arrangement while passing through the penetration point 32 in a manner that reduces the likelihood of trauma to the surrounding skin tissue 30. As the tines 145*a-b* are collectively advanced through the penetration point 32, the free ends of the tines 145*a-b* are moved beneath the dermal skin layers of the skin 30.

When the tines 145*a-b* reach the subcutaneous region, the retainer body 110 can adjusted to the unfolded condition so that the tines 145*a-b* are shifted relative to one another, resulting in the tines 145*a-b* extending outwardly away from one another (as depicted in FIG. 8). During that process of unfolding the retainer body 110, each tine 145*a-b* may optionally retain its generally non-stressed configuration (e.g., the first shape or the steady-state shape). Thus, the anchor device 100 can be installed in accordance with a technique that reduces or eliminates the need to shift the subcutaneous anchors tines 145*a-b* to or from a flexed or stressed configuration during the passage through the skin penetration point 32. As such, the subcutaneous anchors tines 145*a-b* need not undergo substantial flexing during installation or removal, and in some embodiments, the subcutaneous anchors tines 145*a-b* can comprise a generally less costly material (such as stainless steel or biocompatible polymers) rather than more costly materials required for superelastic flexing.

As previously described, the medical device anchor system 10 can secure the medical instrument 20 relative to the skin penetration point 32. With the anchor device 100 positioned such that subcutaneous anchors tines 145*a-b* are in their deployed configuration (FIG. 8), the previously inserted catheter 20 can be releasably secured to the anchor device 100, and to the adapter 180. As shown in FIG. 8, the directional arrow 200 depicts an example motion of manually positioning the catheter 20 adjacent to the medical device anchor system 10 to prepare for the coupling of the catheter 20 onto the medical device anchor system 10. At this stage of the medical device deployment process, the latch assembly 190 is in its open configuration. As such, the anchor device 100 is ready to receive the shaft 26 of the catheter 20.

Referring now to FIG. 9, the catheter 20 is releasably coupled with the medical device anchor system 10 so that the catheter 20 is anchored to the skin penetration point 32. That is, the hub 22 is coupled to the adapter 180, and (optionally) the shaft 26 is coupled to the anchor device 100 using the latch assembly 190. In this embodiment, the hub 22 of the catheter 20 may be removably attached to the adapter 180 using one or more apertures 26*a-b* on the wings 24*a-b* of the hub 22 that mechanically engage with corresponding retention posts 112*a-b* on the adapter 180. Also, the shaft 26 of the catheter 20 can be coupled to the anchor device 100 using the latch assembly 190 as follows (refer also to FIG. 3). With the latch assembly 190 in its open configuration, the shaft 26 of the catheter 20 can be placed onto the surface of the retainer body 110 (e.g., on or near the fold axis 160). Then the hinged portion 191 can be pivoted about hinge 198 to capture the shaft 26 between the surface of the retainer body 110 and the wall of the clearance area 195 of the hinged portion 191. The tab 196 can be used to manipulate the position of the hinged portion 191 as desired. Then the hinged portion 191 can be pressed down onto the retainer body 110 so that the protrusion 193 projects into and latches with the receptacle 194 of the hinged portion 191. Now the shaft 26 is captured between the latch assembly 190 and the retainer body 110. In this fashion, the latch assembly 190 can couple the shaft 26 of the catheter 20 to the anchor device 100.

As shown in FIG. 9, the medical device anchor system 10 releasably retains the catheter 20 in an operative position relative to a portion of skin 30 (e.g., the skin penetration point 32). The medical instrument 20 is mechanically coupled to the anchor device 100 and to the adapter 180, as described above. The anchor device 100, in turn, is anchored to the portion of skin 30 via the anchors 140*a-b* that are deployed into the subcutaneous region. In such embodiments, the medical device anchor system 10 can be secured to the patient without necessarily requiring sutures or adhesive tapes bonded to the skin 30. A shaft 26 of the catheter 20 penetrates a skin penetration point 32 and distally extends into the subcutaneous layers. In this view, it can be seen that some embodiments of the medical device anchor system 10 can enable the distal end of the hub 22 to be positioned some distance away from the skin penetration point 32. Such a configuration provides a compact medical device anchor system 10 that is convenient to install and maintain. For example, the cleaning of the skin 30 around the skin penetration point 32 can be made more convenient by locating the hub 22 remotely from the skin penetration point 32. That is, in general the shaft 26 of the catheter 20 tends to be more flexible and maneuverable than the hub 22. Therefore, locating the hub 22 away from the skin penetration point 32 can, in some cases, enable convenient cleaning of the skin 30 (e.g., the skin 30 under the anchor device 100).

By virtue of the optional sloped nose region 130 of the anchor device 100, the shaft 26 of the catheter 20 may be inclined at an angle in relation to the skin surface 30. The sloped nose region 130 can be declined relative to the generally planar upper surfaces of the retainer body 110 such that the sloped nose region 130 slopes downward in a distal direction towards the skin penetration point 32. Such an orientation between the hub 22 and the skin 30 may, in some circumstances, reduce the stresses applied to the skin penetration point 32 of the patient by the shaft 26 of the catheter 20.

The medical device anchor system 10 provided herein can also tend to reduce stresses that may otherwise be exerted on the shaft 26 when the catheter 20 is manipulated during installation, cleaning around the penetration point 32, or unintended pulling/withdrawal forces. For example, when the hub 22 or proximal portion 28 of the catheter 20 is manipulated in a manner that applies a pulling force (e.g., that might urge the catheter 20 to withdrawn), the force associated with that manipulation are transferred to the adapter 180 because the hub 22 is coupled to the adapter 180. At least some of the force transferred to the adapter 180 can be, in turn, transferred via the tether 170 to the anchor device 100, which in turn, can transfer the forces to the patient's skin 30 via that anchors 140*a-b*. In this fashion, the shaft 26 of the catheter 20 can be protected from some pulling or withdrawal forces. This feature can be beneficial, especially when using catheters with small, fragile, or ultra-compliant distal shafts 26 that could be damaged if exposed to tensile forces from manipulation of the hub 22 or proximal portion 28 of the catheter 20.

In some embodiments, some components of the medical device anchor system 10 can be provided in a sterilized kit that pairs a particular type of catheter 20 or other medical instrument with a corresponding medical device anchor system 10. The particular type of catheter 20 or other medical instruments in the kit can be compatible for releasably mating with the anchor device 100 and the adapter 180 in the kit. In some embodiments, each kit can include one or more medical device anchor systems 10 and the particular type of catheter 20 or other medical instrument enclosed within a flexible packaging material, which preferably includes indicators that identify the type of catheter 20 or other medical instruments that is provided along with instructions for deploying and removing the medical device anchor system 10. The kit may include a one-to-one ratio for the quantity of medical device anchor systems 10 to the quantity of catheters 20. In other embodiments, the kit may include multiple anchor devices 100 (e.g., having differently sized or shaped tines 145*a*-*b*) and/or adapters 180 for each catheter 20 contained therein.

Alternatively, in some embodiments, the medical device anchor system 10 or the components thereof can be provided in individual, sterilized packets so that a practitioner can readily open such a packet and access the selected medical device anchor system 10 or component prior to insertion into the skin penetration point. Such individual packets can include a single medical device anchor system 10 enclosed within a flexible packaging material, which preferably includes indicators that identify the types of catheters or other medical instruments that are compatible for releasably mating with the anchor device 100 and the adapter 180. As such, a practitioner can readily select a packet containing an appropriately sized anchor device 100 and/or adapter 180 for use after the type of catheter or medical instrument is selected for a particular patient.

A number of embodiments of the invention have been described. Nevertheless, it will be understood that various modifications may be made without departing from the scope of the invention. Accordingly, other embodiments are within the scope of the following claims.

What is claimed is:

1. A method of using a medical anchor system, the method comprising:
    deploying subcutaneous anchors of a medical anchor system through a skin penetration point that is occupied by a medical instrument, the subcutaneous anchors being deployed in a subcutaneous region along an underside of a skin layer proximate to the skin penetration point, the subcutaneous anchors extending distally from a distal end of a retainer body of the medical anchor system so that a tether member attached to the retainer body is coupled with the subcutaneous anchors and extends in a longitudinal direction away from a proximal end of the retainer body; and
    securing a first external portion of the medical instrument to a second body of the medical anchor system that is spaced proximally away from the retainer body and tethered to the retainer body via the tether member such that the tether member is positioned between a distal end of the second body member and the proximal end of the retainer body.

2. The method of claim 1, further comprising securing a second external portion of the medical instrument to the retainer body of the medical anchor system, wherein the medical instrument is anchored to the skin penetration point via the subcutaneous anchors of the medical anchor system.

3. A method of using a medical anchor system, the method comprising:
    deploying subcutaneous anchors of a medical anchor system through a skin penetration point that is occupied by a medical instrument, the subcutaneous anchors being deployed in a subcutaneous region along an underside of a skin layer proximate to the skin penetration point, the subcutaneous anchors extending distally from a distal end of a retainer body of the medical anchor system;
    securing a first external portion of the medical instrument to a second body of the medical anchor system, the second body being tethered to the retainer body via a flexible member that extends proximally away from a proximal end of the retainer body; and
    trimming the flexible member to remove an excess length of the flexible member that extends proximally away from the second body of the medical anchor system.

4. The method of claim 2, wherein securing the second external portion of the medical instrument to the retainer body comprises adjusting a latch assembly to a closed position to mate with the medical instrument.

5. The method of claim 1, wherein securing a first external portion of the medical instrument to the second body comprises releasably mating one or more engagement portions of the second body with one or more corresponding elements of the medical instrument.

6. The method of claim 5, wherein the one or more engagement portions each comprise a retention post that extends from the second body.

7. The method of claim 1, wherein deploying subcutaneous anchors of a medical anchor system through a skin penetration point comprises installing the subcutaneous anchors into the skin penetration point while the subcutaneous anchors remain substantially unstressed.

8. A method of using a medical anchor system, the method comprising:
    deploying subcutaneous anchors of a medical anchor system through a skin penetration point that is occupied by a medical instrument, the subcutaneous anchors being deployed in a subcutaneous region along an underside of a skin layer proximate to the skin penetration point, the subcutaneous anchors extending distally from a distal end of a retainer body of the medical anchor system; and
    securing a first external portion of the medical instrument to a second body of the medical anchor system, the second body being tethered to the retainer body via a flexible member that extends proximally away from a proximal end of the retainer body, wherein the flexible member is connected to and extends proximally away from the proximal end of the retainer body.

9. The method of claim 8, wherein the flexible member is directly connected to the retainer body so that a distal end of the flexible member is permanently maintained in a fixed position relative to the subcutaneous anchors that extend distally from the distal end of the retainer body.

10. The method of claim 3, wherein the second body directly contacts and mates with an exterior of the medical instrument at a mating location proximally spaced away from the proximal end of the retainer body.

11. The method of claim 1, wherein the tether member is integrally formed with the retainer body.

12. The method of claim 1, wherein the tether member defines a plurality of mating locations spaced apart at different longitudinal positions relative to the proximal end of the retainer body.

13. The method of claim 12, wherein the second body is releasably and directly matable to the tether member at any of the plurality of mating locations.

14. A method of using a medical anchor system, the method comprising:

deploying subcutaneous anchors of a medical anchor system through a skin penetration point that is occupied by a medical instrument, the subcutaneous anchors being deployed in a subcutaneous region along an underside of a skin layer proximate to the skin penetration point, the subcutaneous anchors extending distally from a distal end of a retainer body of the medical anchor system; and securing a first external portion of the medical instrument to a second body of the medical anchor system, the second body being tethered to the retainer body via a flexible member that extends proximally away from a proximal end of the retainer body, wherein the flexible member has a length between the proximal end of the retainer body and the distal end of the second body between 2 cm and 6 cm.

15. A method of using a medical anchor system, the method comprising:

deploying subcutaneous anchors of a medical anchor system through a skin penetration point that is occupied by a medical instrument, the subcutaneous anchors being deployed in a subcutaneous region along an underside of a skin layer proximate to the skin penetration point, the subcutaneous anchors extending distally from a distal end of a retainer body of the medical anchor system so that a flexible tether member attached to the retainer body is coupled with the subcutaneous anchors and extends in a longitudinal direction away from a proximal end of the retainer body;

securing a second body to the flexible tether member such that the flexible tether member is positioned between a distal end of the second body member and the proximal end of the retainer body, the second body being tethered to the retainer body and spaced away from the proximal end of the retainer body; and securing a first external portion of the medical instrument to the second body of the medical anchor system by releasably mating one or more engagement portions of the second body with one or more corresponding elements of the medical instrument.

16. The method of claim 15, wherein the flexible tether member is directly connected to the retainer body so that a distal end of the flexible tether member is permanently maintained in a fixed position relative to the subcutaneous anchors that extend distally from the distal end of the retainer body.

17. A method of using a medical anchor system, the method comprising:

deploying subcutaneous anchors of a medical anchor system through a skin penetration point that is occupied by a medical instrument, the subcutaneous anchors being deployed in a subcutaneous region along an underside of a skin layer proximate to the skin penetration point, the subcutaneous anchors extending distally from a distal end of a retainer body of the medical anchor system;

securing a second body to a flexible member that extends proximally away from a proximal end of the retainer body such that the second body is tethered to the retainer body and spaced away from the proximal end of the retainer body, wherein the flexible member is directly connected to the retainer body so that a distal end of the flexible member is permanently maintained in a fixed position relative to the subcutaneous anchors that extend distally from the distal end of the retainer body; and securing a first external portion of the medical instrument to the second body of the medical anchor system by releasably mating one or more engagement portions of the second body with one or more corresponding elements of the medical instrument, wherein the second body directly contacts and mates with an exterior of the medical instrument at a mating location proximally spaced away from the proximal end of the retainer body.

18. The method of claim 17, wherein the flexible member defines a plurality of mating locations spaced apart at different longitudinal positions relative to the proximal end of the retainer body.

19. The method of claim 18, wherein the second body is releasably and directly matable to the flexible member at any of the plurality of mating locations.

20. The method of claim 19, further comprising trimming the flexible member to remove an excess length of the flexible member that extends proximally away from the second body of the medical anchor system.

21. The method of claim 14, further comprising securing a second external portion of the medical instrument to the retainer body of the medical anchor system, wherein the medical instrument is anchored to the skin penetration point via the subcutaneous anchors of the medical anchor system.

22. The method of claim 21, wherein securing the second external portion of the medical instrument to the retainer body comprises adjusting a latch assembly to a closed position to mate with the medical instrument.

23. The method of claim 14, wherein securing a first external portion of the medical instrument to the second body comprises releasably mating one or more engagement portions of the second body with one or more corresponding elements of the medical instrument.

24. The method of claim 23, wherein the one or more engagement portions each comprise a retention post that extends from the second body.

* * * * *